(12) United States Patent
Karpiel

(10) Patent No.: US 7,314,481 B2
(45) Date of Patent: Jan. 1, 2008

(54) STENT INTRODUCER APPARATUS

(75) Inventor: John Karpiel, Winston-Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 480 days.

(21) Appl. No.: 10/449,730

(22) Filed: May 30, 2003

(65) Prior Publication Data

US 2004/0010265 A1    Jan. 15, 2004

Related U.S. Application Data

(60) Provisional application No. 60/384,943, filed on May 31, 2002.

(51) Int. Cl.
    *A61F 2/04* (2006.01)

(52) U.S. Cl. ............... 623/1.12; 623/1.11; 604/164.05; 600/585

(58) Field of Classification Search ............... 623/1.11; 606/194
    See application file for complete search history.

(56) References Cited

U.S. PATENT DOCUMENTS

| | | | |
|---|---|---|---|
| 4,306,562 A | 12/1981 | Osborne | |
| RE31,855 E | 3/1985 | Osborne | |
| 4,581,025 A | 4/1986 | Timmermans | |
| 4,772,266 A | 9/1988 | Groshong | |
| 4,997,424 A * | 3/1991 | Little | ......................... 604/161 |
| 5,120,299 A | 6/1992 | Lombardi | |
| 5,158,545 A | 10/1992 | Trudell et al. | |
| 5,167,634 A | 12/1992 | Corrigan, Jr. et al. | |
| 5,201,757 A * | 4/1993 | Heyn et al. | .................. 606/198 |
| 5,221,263 A | 6/1993 | Sinko et al. | |
| 5,222,970 A | 6/1993 | Reeves | |
| 5,250,033 A | 10/1993 | Evans et al. | |
| 5,320,602 A | 6/1994 | Karpiel | |
| 5,415,639 A | 5/1995 | VandenEinde et al. | |
| 5,425,717 A | 6/1995 | Mohiuddin | |
| 5,441,504 A | 8/1995 | Pohndorf et al. | |
| 5,489,273 A | 2/1996 | Whitney et al. | |
| 5,534,007 A * | 7/1996 | St. Germain et al. | ...... 623/1.11 |
| 5,536,255 A | 7/1996 | Moss | |

(Continued)

FOREIGN PATENT DOCUMENTS

WO    WO 98/20812    5/1998

(Continued)

*Primary Examiner*—Glenn K. Dawson
(74) *Attorney, Agent, or Firm*—Brinks Hofer Gilson & Lione

(57) ABSTRACT

A stent introducer apparatus includes a handle with a proximal end and a distal end and having a portion that is coaxially slidable from the distal end to the proximal end and vice versa. A catheter having a proximal end and a distal end is provided with a pair of open end slits each of which defines a tab that is connected to the slidable portion of the handle. A guide wire is disposed within the catheter and has a proximal end and a distal end such that when the slidable portion of the handle is moved from the distal end to the proximal end, the distal end of the guide wire is exposed. The guide wire has a stent carrying portion at its distal end to carry a stent that is deployed when the distal end of the guide wire is exposed.

18 Claims, 3 Drawing Sheets

U.S. PATENT DOCUMENTS

| | | |
|---|---|---|
| 5,591,226 A | 1/1997 | Trerotola et al. |
| 5,630,830 A | 5/1997 | Verbeek |
| 5,735,819 A | 4/1998 | Elliott |
| 5,766,203 A * | 6/1998 | Imran et al. ............... 623/1.11 |
| 5,800,414 A | 9/1998 | Cazal |
| 5,951,518 A | 9/1999 | Licata et al. |
| 6,210,366 B1 | 4/2001 | Sanfilippo, II |
| 6,221,081 B1 | 4/2001 | Mikus et al. |
| D450,839 S | 11/2001 | Junker |
| 2002/0165554 A1 | 11/2002 | Dworschak et al. |

FOREIGN PATENT DOCUMENTS

| | | |
|---|---|---|
| WO | WO 01/10345 A1 | 2/2001 |

* cited by examiner

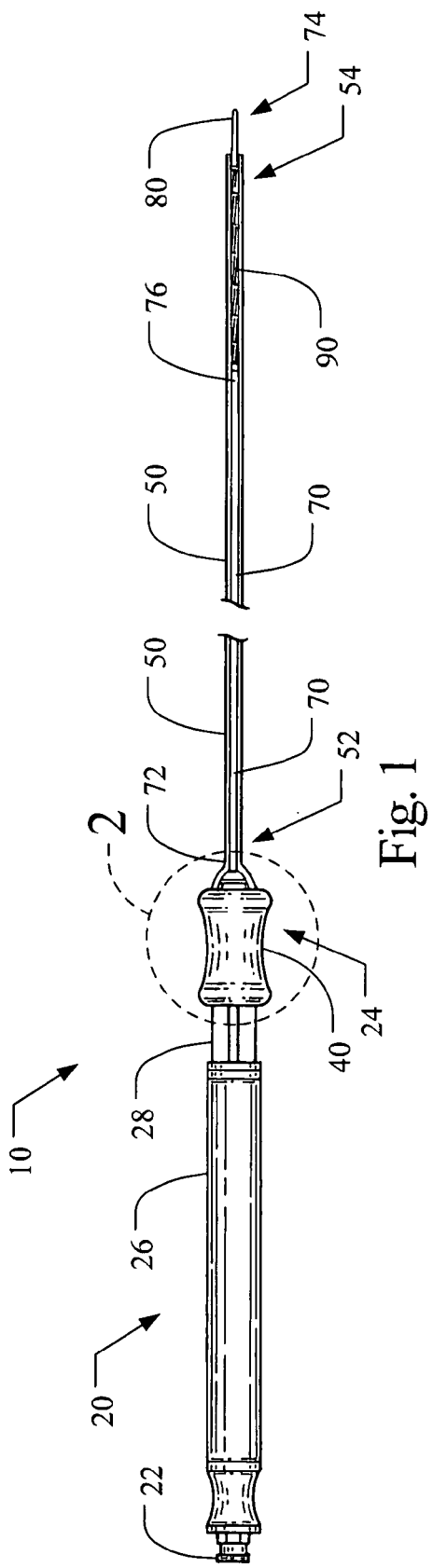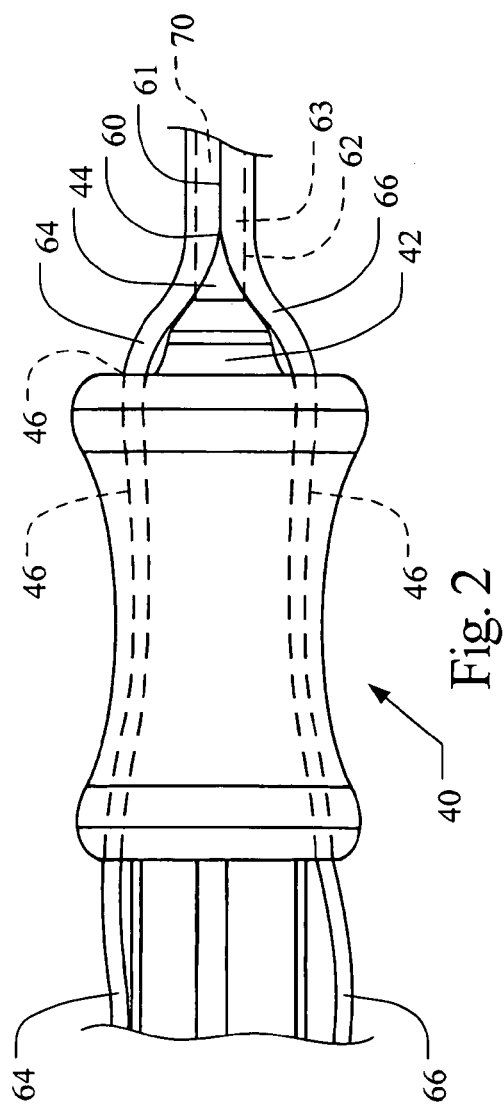

STENT INTRODUCER APPARATUS

RELATED APPLICATIONS

This application claims the benefit of U.S. Provisional Application No. 60/384,943, filed May 31, 2002, and entitled "Stent Introducer Apparatus".

TECHNICAL FIELD

The present invention relates to an apparatus for delivering an implantable prosthesis and, in particular, to an apparatus for introducing a stent to a desired location.

BACKGROUND OF THE INVENTION

Stents are used for a variety of applications. For example, stents are used within the biliary tree. Current biliary and pancreatic stent delivery systems generally include an introducer catheter with the stent loaded at the distal end thereof. A pusher catheter is used to deploy the stent from the distal end of the introducer catheter.

While current stent delivery systems are effective, there is a continuing need for a more effective and efficient stent delivery system. The present invention meets that need by providing an apparatus that ensures that the stent does not jump forward during deployment, and also provides enhanced accuracy of the stent deployment location.

SUMMARY OF THE INVENTION

Accordingly, the stent introducer apparatus has an introducer catheter with a proximal end and a distal end, the distal end providing a self-expanding stent. The proximal end of the introducer catheter has a pair of open-ended slits that have a closed end between the catheter proximal end and the distal end. The pair of open-ended slits define a first tab on a first side of the introducer catheter and a second tab on a second side of the introducer catheter. A guide wire is disposed within the catheter and has a proximal end and a distal end, the distal end including a stent-carrying section. When the first and second tabs are moved toward the proximal end of the guide wire, the distal end of the guide wire is exposed to deploy the stent.

Advantageously, when the first and second tabs are moved toward the proximal end, the slits will propagate in a direction toward the distal end of the introducer catheter. To facilitate the propagation of the slit, the stent introducer apparatus is provided with an adapter. In one embodiment, the adapter comprises a tubular section that surrounds the guide wire and has one end that contacts the slits.

In another embodiment of the present invention, the stent introducer apparatus has a handle with a proximal end, a distal end and a slidable portion. The stent introducer apparatus also has an introducer catheter with a proximal end with tabs extending from the proximal end and attached to the slidable portion of the handle. The introducer catheter also has a distal end from which a preloaded self-expanding stent can be deployed when the slidable handle is moved coaxially (i.e., from the distal end to the proximal end). Preferably, a guide wire is disposed within the catheter. The guide wire has a proximal end and a distal end, the distal end including a stent-carrying section.

The handle preferably has an outer portion and an inner portion such that the outer portion is slidably received on the inner portion along a coaxial direction. Accordingly, the outer portion can move coaxially from the distal end of the handle to the proximal end of the handle. The inner portion of the handle is in contact with the guide wire so that when the outer portion of the handle is moved from the distal end to the proximal end of the handle, the catheter likewise moves toward the proximal end of the handle and, as a result, exposes the distal end of the guide wire to thereby deploy the stent.

The distal end of the handle may be provided with an adapter that facilitates the travel of the catheter in the proximal direction. The adapter may have a nose that is tapered at its distal end to provide a surface for parting the catheter and to provide a surface that better engages the proximal end of the guide wire. The adapter may also be provided with a push rod that engages the proximal end of the guide wire.

As noted above, the proximal end of the catheter has a pair of tabs that are defined by a pair of slits provided on opposite sides of the catheter. Each slit has a closed end. The tabs are connected to the slidable portion of the handle and, preferably, are connected to the outer portion of the handle. The tabs may be connected to the inside or the outside of the outer portion of the handle depending on manufacturing and aesthetic requirements. When an adapter is provided, it may be useful to provide guide slots in the adapter through which a portion of the tabs pass. By providing such a structure, the movement of the catheter relative to the guide wire may be enhanced by propagating the longitudinal slits.

In operation, as the outer portion of the handle is retracted or moved from the distal end to the proximal end (i.e., in a proximal direction), the catheter travels toward the proximal end of the handle while each slit tears longitudinally at the closed ends toward the distal end of the catheter. The distal end of the guide wire is exposed as a result of the proximal movement of the catheter so as to deploy the stent. The tear in the catheter will propagate the distance that the handle is retracted, which will in turn correspond to the distance that the distal end of the guide wire is exposed. This distance is preferably about the length of a stent.

BRIEF DESCRIPTION OF THE DRAWINGS

FIG. 1 is a partially sectioned side view of one embodiment of the present invention.

FIG. 2 is an enlarged view of a portion of the embodiment of FIG. 1.

DESCRIPTION OF THE INVENTION

Figure 3:
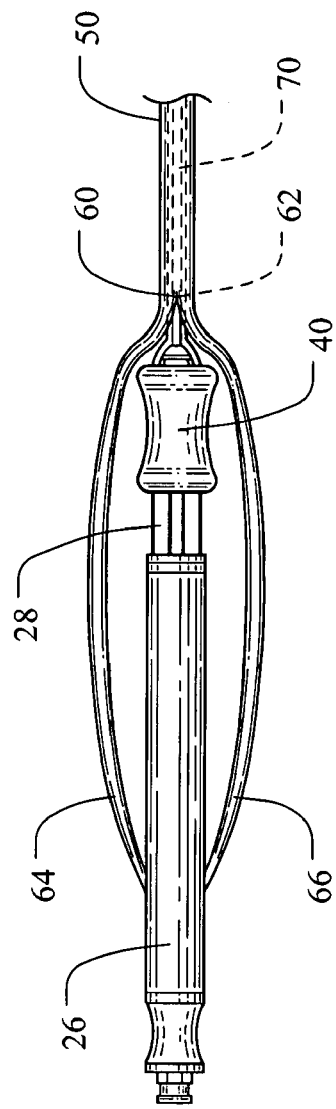
FIG. 3 is a side view of another embodiment of the present invention.

Turning now to FIG. 1, one embodiment of the stent introducer apparatus 10 according to the present invention is shown. The stent introducer apparatus 10 includes a handle 20, an introducer catheter 50, a guide wire 70 and a stent 90. The handle has a portion that is slidable such that when the slidable portion of the handle slides from a distal end 24 to a proximal end 22 (i.e., in a distal direction), the catheter proximal end 52 also travels toward the handle proximal end 22, thereby causing a stent 90 that is preloaded onto the guide wire 70 (disposed within the catheter 50) to be exposed and deployed. While the type of stent is not critical to the invention, preferred stents are the self-expanding biliary stent sold as SPIRAL Z™ and ZA-STENT™ sold by Wilson-Cook Medical, Inc.

The handle 20 has a proximal end 22 and a distal end 24. The handle 20 also has a slidable portion that can slide coaxially from the distal end 24 to the proximal end 22 and vice versa. In one embodiment, the handle comprises an outer portion 26 and an inner portion 28, with the outer portion 26 slidable over the inner portion 28.

The catheter 50 has a proximal end 52 and a distal end 54. As best seen in FIG. 2, the catheter proximal end 52 is slit longitudinally to produce a first slit 60 and a second slit 62 to respectively define a first tab 64 and a second tab 66. The first tab 64 is located on one side of the catheter 50 while the second tab 66 is located on the other or opposite side of the catheter. Each slit 60, 62 extends to a respective closed end 61, 63 that is located between the proximal end 52 and the distal end 54 of the catheter 50.

As noted above, the first 64 and second 66 tabs are each attached to the slidable portion of the handle 20 and, in particular to the handle outer portion 26. The tabs 64, 66 may be attached to the inside of the outer portion 26 or, as best seen in FIG. 3, to the outside of the outer portion 26.

Referring back to FIG. 1, the catheter 50 may be made from any suitable material and is preferably made from a clear material such as a substantially clear polymer. Suitable materials include, but are not limited to, polytetrafluoroethylene (PTFE) and polyeretherketone (PEEK). The catheter 50 can comprise a thin-walled tube of a longitudinally molecularly oriented, anisotropic material such as PTFE whose molecular properties permit it to be torn longitudinally along a predetermined split line. A method for molecularly orienting is disclosed in U.S. Pat. No. 4,306,562, the relevant contents of which are incorporated herein by reference. Alternatively, longitudinal tearing can be accomplished by pre-weakening the sheath by the formation of one or more grooves or the like in the wall of the sheath so that the sheath tears along the grooves.

A guide wire 70 is preferably provided within the catheter 50. The guide wire 70 has a proximal end 72 and a distal end 74. The distal end 74 is provided with a stent-carrying section 76. Preferably, the stent-carrying section 76 has an outside diameter smaller than the outside diameter of the adjacent or other portions of the guide wire 70 so that when the stent 90 is loaded onto the stent-carrying section 76, the resulting thickness or diameter of the stent 90 and stent-carrying section 76 is not greater than the diameter of the adjacent portion of the guide wire 70. By dimensioning the guide wire 70 in this fashion, the catheter 50 will more easily travel over the stent 90 when the catheter 50 is being retracted or pulled in the proximal direction.

The guide wire 70 may be made of any suitable material such as PEEK, polyvinyl chloride (PVC), polyimide, polyimide reinforced with a stainless steel braid, polyurethane, nylon, metal tubing such as nitinol or stainless steel, and the like. The guide wire 70 may also be formed as a coil or a solid-core wire guide. In one embodiment, a substantial portion of the guide wire 70 is formed from nylon tubing while the distal portion, and especially the stent-carrying section, is formed from polyimide.

Figure 4:
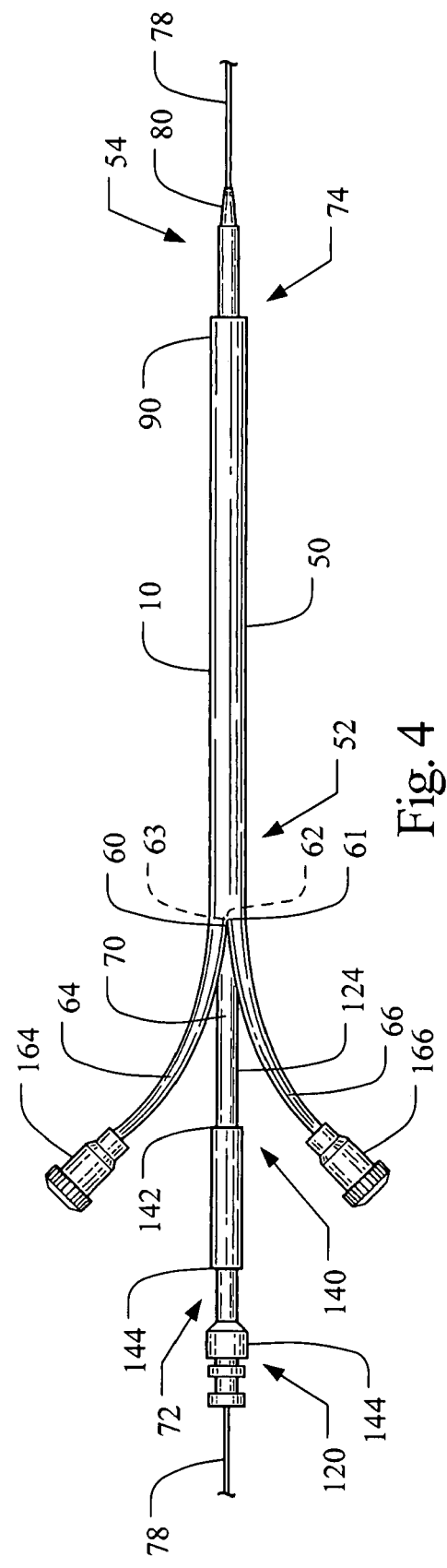
FIG. 4 is a side view of another embodiment of the present invention.

It should be understood by those skilled in the art that the guide wire 70 could comprise an inner sheath or catheter, often referred to as a pusher member, with a lumen extending longitudinally through the interior thereof. In such embodiments, the inner catheter would be movably disposed within the catheter 50, and the inner catheter would comprise a stent-carrying section on the distal end portion thereof. As shown in FIG. 4, a separate guide wire 78 would extend through the inner catheter. The separate guide wire 78, which extends through the entire length of the introducer apparatus 10, may be employed by the user to navigate the internal body lumen of the patient. As understood by those skilled in the art, guide wire 78 could be made of any suitable material or comprise any of the features described above in connection with wire guide 70.

A tip 80 formed of a soft material such as a soft polymer with good bonding properties is provided so that it can be bonded or attached to the catheter distal end 74 of the guide wire 54. Preferably, the tip 80 and the catheter distal end 74 are tapered and/or rounded to facilitate an atraumatic entry into a body lumen. The tip 80 may include barium sulfate or some other agent or marker to provide radiopacity.

In a preferred embodiment, the handle distal end 24 is provided with an adapter 40 that contacts the guide wire proximal end 72 and also provides a surface over which a portion of the tabs 64, 66 of the catheter 50 will pass to more easily propagate the slits 60, 62 in the catheter 50 in a longitudinal direction. In this embodiment, and as best seen in FIG. 2, the adapter 40 has a nose 42 that may further be provided with a push rod 44. Desirably, the push rod 44 has approximately the same diameter as the guide wire 70 so that substantial contact will be made between the ends of the push rod 44 and the guide wire 70.

In the embodiment where the apparatus is provided with an adapter 40, it is preferred that the adapter 40 has a pair of guide slots 46 that receive a respective portion of the tabs 64, 66. By providing the guide slots 46, the tabs 64, 66 are less likely to become tangled or obstructed as the tabs 64, 66 are pulled in the proximal direction relative to the guide wire 70. The guide slots 46 likewise reduce the likelihood that the tabs 64, 66 will interfere with a user's ability to grasp the adapter 40. In addition, the propagation of the slits 60, 62 is enhanced by maintaining the separation of the tabs.

Operation of the apparatus will now be described. The catheter distal end 54 is delivered to the desired location. Once the catheter distal end 54 is in the correct position for deployment of the stent 90, the slidable portion of the handle 20 is retracted in a proximal axial direction (i.e., pulled from the distal end toward the proximal end). This action pulls the proximal end of the catheter 52 toward the proximal end of the handle 22, which thereby causes the distal end of the handle 24 to contact and propagate the slits 60, 62 in the direction toward the distal end 54 of the catheter 50. Because the catheter 50 is traveling toward the proximal end of the handle 22, and because the guide wire 70 is prevented from traveling by contact with the distal end of the handle 24, the distal end of the guide wire 74 becomes exposed. In turn, the stent 90 becomes exposed and obtains a deployed position. Thereafter, the catheter 50 and guide wire 70 can be retracted from the desired location, leaving the deployed stent 90 behind.

Referring now to FIG. 4, an alternative embodiment of the present invention is shown. In this embodiment the handle 20 described above is not required. Instead, a handle 120 is provided at the proximal end of the guide wire 72. The handle 120 may be formed of any suitable material and its construction is not critical. The handle 120 is provided so that the user will be able to securely hold the guide wire 70 when it is desired to deploy the stent 90.

In addition, the tabs 64, 66 are provided with knobs 164, 166 respectively. The knobs 164, 166 are known in the art and may simply be a knob that screws into a socket. The force between the screw and the socket maintains the end of the tab in position. The knobs 164, 166 are provided to allow the user to firmly grasp the tabs 64, 66 when it is desired to deploy the stent 90.

An adapter 140 is provided to aid in propagating the slits 60, 62 in the longitudinal direction toward the distal end of the catheter 54. In this embodiment, the adapter 140 has a distal end 142 and a proximal end 144, with the proximal end 144 being adjacent the proximal end of the guide wire 72. The adapter 140 surrounds a portion of the guide wire 70 near the proximal end of the guide wire 72. The adapter 140 is immovable with respect to the guide wire 70 and is preferably a material that is compatible with the other materials used in the construction of the apparatus of the present invention.

To deploy the stent 90 using this embodiment of the present invention, the distal end of the catheter 54 is delivered to the desired location. Once the distal end of the catheter 54 is in the correct position for deployment of the stent 90, one person grasps the handle 120 while another person grasps each of the knobs 164, 166 and pulls the knobs toward the proximal end of the guide wire 72. This action pulls the proximal end of the catheter 52 toward the handle 20 and contact with the distal end of the handle 124, which in turn causes the slits 60, 62 to propagate in the direction toward the distal end of the catheter 54. Because the catheter 50 is traveling toward the proximal end of the handle 122, and because the guide wire 70 is prevented from traveling, the distal end of the guide wire 74 becomes exposed. In turn, the stent 90 becomes exposed and obtains a deployed position. Thereafter, the catheter 50 and guide wire 70 can be retracted from the desired location, leaving the stent 90 behind.

Figure 5:
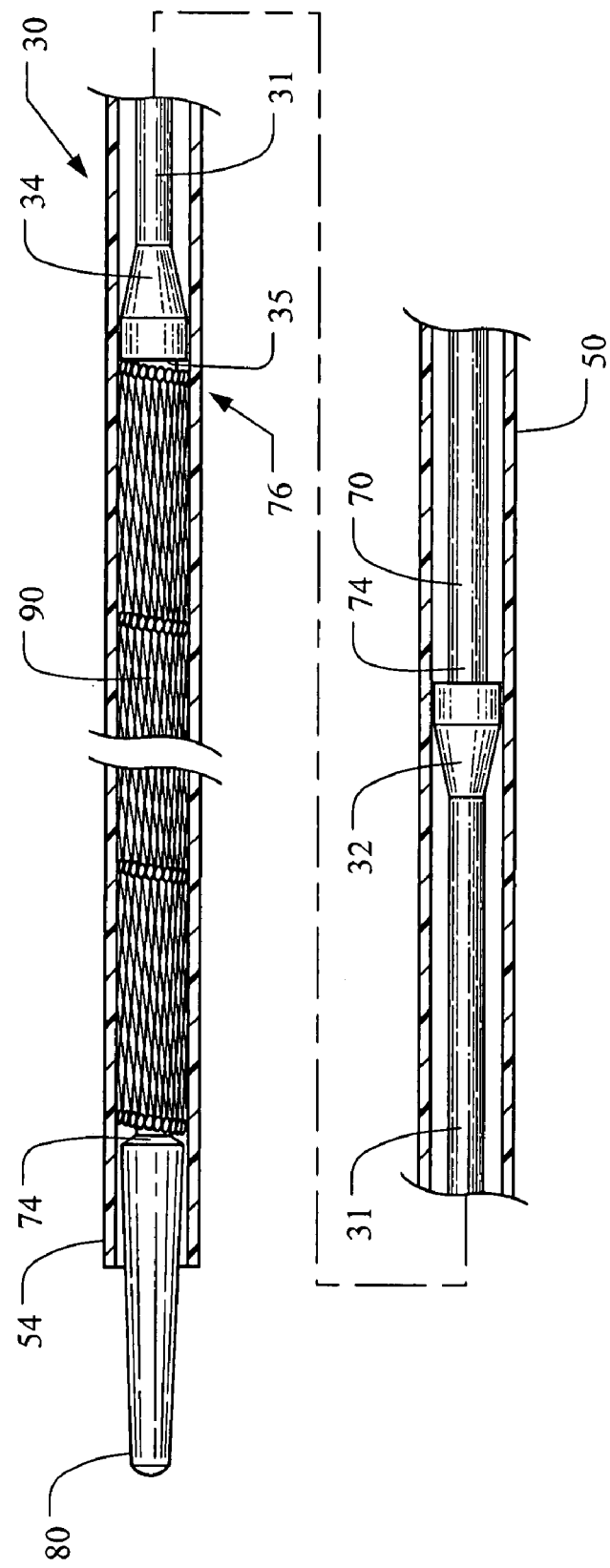
FIG. 5 is a partially sectioned view of the distal end of a stent apparatus that may be used with any of the stent apparatus of the present invention.

Turning now to FIG. 5, a partial section view of the distal end of one embodiment of the apparatus of the present invention is shown. In particular, a pusher assembly 30 is shown. The pusher assembly 30 includes a tubular portion 31 that has one end connected to the distal end 74 of the guide wire 70 preferably through a tapered portion 32. The other end of the tubular portion 31 includes a pusher head 34 that contacts the stent 90 to push the stent 90 from the introducer catheter 50.

The pusher head 34 and the tapered portion may be formed of a separate material or may be integral with the tubular portion 31. Where it is formed of a separate material, it may be made of metal or plastic and may be secured to the tubular portion by gluing or other well known securing methods. The pusher head has a broad face 35 to contact one end of the stent 90 to urge the stent 90 forward until the stent 90 is deployed. It should be understood that the pusher assembly 30 can be incorporated into any of the above-described embodiments of the stent introducer apparatus.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

The invention claimed is:

1. A stent introducer apparatus comprising:
    a catheter having a proximal end portion and a distal end portion;
    a guide wire movably disposed within the catheter, the guide wire having a proximal end portion and a distal end portion;
    a deployable stent, the stent being disposed within the distal end portion of the catheter and being engaged by the distal end portion of the guide wire; and
    a handle fixedly connected to the proximal end portion of the guide wire,
    wherein the stent is deployed by moving the catheter in a proximal direction relative to the guide wire, the proximal end portion of the catheter being engaged by and split by the handle as the catheter is moved in the proximal direction,
    wherein the handle comprises a first portion and a second portion, the first portion being axially movably connected to the second portion, further wherein the proximal end portion of the catheter is connected to the first portion and the proximal end portion of the guide wire is connected to the second portion, whereby movement of the first portion relative to the second portion causes the proximal end portion of the catheter to be split by the second portion of the handle.

2. The stent introducer apparatus according to claim 1, wherein the proximal end portion of the catheter comprises one or more tabs connected to the first portion of the handle.

3. The stent introducer apparatus according to claim 2, wherein each of the tabs pass through an opening in the second portion of the handle.

4. The stent introducer apparatus according to claim 1, wherein the second portion comprises an adapter configured to engage and split the proximal end portion of the catheter.

5. The stent introducer apparatus according to claim 4, wherein the adapter comprises a nose configured to separate the proximal end portion of the catheter from the guide wire.

6. The stent introducer apparatus according to claim 5, wherein the nose includes a sloped surface adapted to split the proximal end portion of the catheter into a plurality of tab portions as the catheter is moved in the proximal direction.

7. The stent introducer apparatus according to claim 1, wherein the proximal end portion of the catheter comprises a longitudinally disposed weakened area to facilitate splitting of the catheter by the handle as the catheter is moved in the proximal direction.

8. The stent introducer apparatus according to claim 1, wherein the distal end portion of the guide wire comprises a pusher assembly adapted to engage the stent, the pusher assembly comprising a pusher head adapted to engage a proximal end of the stent.

9. The stent introducer apparatus according to claim 8, wherein the distal end portion of the guide wire further comprises an end cap, said end cap being disposed adjacent to a distal end of the stent.

10. The stent introducer apparatus according to claim 9, wherein the end cap is connected to the pusher assembly by a stent carrying section, the stent carrying section adapted for receiving the stent thereon.

11. The stent introducer apparatus according to claim 1, wherein the stent comprises a self-expanding stent having a compressed configuration and an expanded deployed configuration, the stent assuming the compressed configuration when disposed within the distal end portion of the catheter.

12. The stent introducer apparatus according to claim 1, wherein the guide wire comprises an inner catheter with a lumen extending longitudinally there through.

13. The stent introducer apparatus according to claim 12, further comprising an inner guide wire movably extending through the lumen of the inner catheter.

14. A stent introducer apparatus comprising:
- a catheter having a proximal end portion and a distal end portion,
- a pair of tab portions each having a proximal end and a distal end, the distal ends of the tab portions being connected to the proximal end portion of the catheter;
- a guide wire movably disposed within the catheter, the guide wire having a proximal end portion and a distal end portion;
- a deployable stent, the stent being disposed within the distal end portion of the catheter and being engaged by the distal end portion of the guide wire; and
- a handle having a first portion and a second portion, the first portion being axially movably connected to the second portion, the proximal ends of the tab portions being fixedly connected to the first portion of the handle and the proximal end portion of the guide wire being fixedly connected to the second portion of the handle,
- wherein the second portion of the handle is adapted to engage and split the proximal end portion of the catheter at a location where the distal ends of the tab portions are connected to the proximal end portion of the catheter, and
- wherein the stent is deployed by moving the first portion of the handle in a proximal direction relative to the second portion of the handle so as to cause the proximal end portion of the catheter to be engaged and split by the second portion of the handle, whereby the catheter is moved in a proximal direction relative to the guide wire.

15. The stent introducer apparatus according to claim 14, wherein each of the tabs extend through an opening in the second portion of the handle.

16. The stent introducer apparatus according to claim 14, wherein the proximal end portion of the catheter comprises a longitudinally disposed weakened area to facilitate splitting of the catheter by the second portion of the handle as the catheter is moved in the proximal direction.

17. The stent introducer apparatus according to claim 14, wherein the distal end portion of the guide wire comprises a pusher assembly adapted to engage the stent, the pusher assembly comprising a pusher head adapted to engage a proximal end of the stent and prevent the stent from being axially moved in response to proximal movement of the catheter relative to the guide wire.

18. The stent introducer apparatus according to claim 14, wherein the stent comprises a self-expanding stent having a compressed configuration and an expanded deployed configuration, the stent assuming the compressed configuration when disposed within the distal end portion of the catheter.

* * * * *